US008617854B2

(12) United States Patent
Breuer et al.

(10) Patent No.: US 8,617,854 B2
(45) Date of Patent: Dec. 31, 2013

(54) **METHOD FOR PRODUCING L-PHENYLEPHRINE USING AN ALCOHOL DEHYDROGENASE OF *AROMATOLEUM AROMATICUM* EBN1 (*AZOARCUS* SP. EBN1)**

(75) Inventors: Michael Breuer, Darmstadt (DE);
Andreas Pletsch, Limburgerhof (DE);
Bernhard Hauer, Fussgoenheim (DE);
Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/063,630

(22) PCT Filed: Sep. 15, 2009

(86) PCT No.: PCT/EP2009/061974
§ 371 (c)(1),
(2), (4) Date: Mar. 11, 2011

(87) PCT Pub. No.: WO2010/031776
PCT Pub. Date: Mar. 25, 2010

(65) Prior Publication Data
US 2011/0171700 A1 Jul. 14, 2011

(30) Foreign Application Priority Data
Sep. 17, 2008 (EP) ..................... 08164488

(51) Int. Cl.
C12P 7/22 (2006.01)
C12P 13/00 (2006.01)

(52) U.S. Cl.
USPC .......................................... 435/128; 435/156

(58) Field of Classification Search
None
See application file for complete search history.

(56) References Cited

U.S. PATENT DOCUMENTS

| 4,310,702 A | 1/1982 | Masilamani et al. |
| 5,710,341 A * | 1/1998 | Siegel et al. .................. 568/316 |
| 6,187,956 B1 | 2/2001 | Klinger et al. |
| 7,785,847 B2 * | 8/2010 | Sturmer et al. ............... 435/156 |
| 2008/0206824 A1 | 8/2008 | Sturmer et al. |
| 2009/0325225 A1 | 12/2009 | Breuer et al. |
| 2010/0143991 A1 | 6/2010 | Breuer et al. |

FOREIGN PATENT DOCUMENTS

| CN | 101503714 A | 8/2009 |
| EP | 0735016 A1 | 10/1996 |
| WO | WO-00/43345 A1 | 7/2000 |
| WO | WO-2005/108590 A2 | 11/2005 |
| WO | WO-2006/094945 A2 | 9/2006 |
| WO | WO-2007/147897 A1 | 12/2007 |
| WO | WO-2008/055988 A2 | 5/2008 |

OTHER PUBLICATIONS

Hettche PDP: Mashine english translation of WO2007/147897.*
Guy, A., et al., "Selective α-Chlorination of Alkyl Aryl Ketones," Synthesis, vol. 12, pp. 1018-1020 (1982).
Kajigaeshi, S., et al., "α-Chlorination of Aromatic Acetyl Derivatives with Benzyltrimethylammonium Dichloroiodate," Synthesis, vol. 7, pp. 545-546 (1988).
Sakuraba, S., et al., "Efficient Asymmetric Hydrogenation of ∝-Amino Ketone Derivatives. A Highly Enantioselective Synthesis of Phenylephrine, Levamisole, Carnitine and Propranolol)," Chem. Pharm. Bull., vol. 43, No. 5, pp. 738-747 (1995).
Takeda, H., et al., "Practical Asymmetric Synthesis of (R)-(-)-Phenylephrine Hydrochloride Catalyzed by (2R,4R)-MCCPM-Rhodium Complex)" Tetrahedron Letters, vol. 30, pp. 367-670 (1989).
Yang, Y., et al., "Enzymatic ketone reduction: mapping the substrate profile of a short-chain alcohol dehydrogenase (YMR226c) from *Saccharomyces cerevisiae*," Tetrahedron: Asymmetry, vol. 18, pp. 1799-1803 (2007).
Rabus, R., et al., "The Genome Sequence of an Anaerobic Aromatic-Degrading Denitrifying Bacterium, Strain EbN1", Arch. Microbiol., 2005, vol. 183, pp. 27-36.
Gröger, H., et al. "Preparative Asymmetric Reduction of Ketones in a Biphasic Medium with an (S)-Alcohol Dehydrogenase under In Situ-Cofactor-Recycling with a Formate Dehydrogenase", Tetrahedron, 2004, vol. 60, pp. 633-640.
Hummel, W., "Large-Scale Applications of NAD(P)-Dependent Oxidoreductases: Recent Developments", Trends in Biotechnol., 1999, vol. 17, pp. 487-492.
Bradshaw, C. W., et al. "*Lactobacillus kefir* Alcohol Dehydrogenase: A Useful Catalyst for Synthesis", J. Org. Chem., 1992, vol. 57, No. 5, pp. 1532-1536.
"Short-Chain Dehydrogenase/Reductase, Possibly Involved in Polyhydroxybutyrate (PHB) Synthesis", UniProt Database Accession No. Q5P1L5, Jan. 4, 2005.
Fantin, G., et al., "Anti-Prelog Microbial Reduction of Prochiral Carbonyl Compounds", Tetrahedron, 1996, vol. 52, No. 10, pp. 3547-3552.
Zheng, Z., et al., "Thioesterase II of *Escherichia coli* Plays an Important Role in 3-Hydroxydecanoic Acid Production", Applied and Environmental Microbiology, 2004, vol. 70, No. 7, pp. 3807-3813.

* cited by examiner

Primary Examiner — Tekchand Saidha
Assistant Examiner — Md. Younus Meah
(74) Attorney, Agent, or Firm — Novak Druce Connolly Bove + Quigg LLP

(57) ABSTRACT

The present invention relates to a multi-stage process for producing substituted, optically active alcohols, comprising an enzyme-catalyzed synthesis step, in particular a synthesis step which is catalyzed by an alcohol dehydrogenase. The inventive method is particularly suitable for producing phenylephrine, i.e. 3-[(1R)-1-hydroxy-2-methylamino-ethyl]-phenol.

12 Claims, 1 Drawing Sheet

SEQ ID NO:1 Nucleic acid sequence of the phenylethanol dehydrogenase from *Azoarcus* sp EbN1 (GenBank ID 25956124, Region: 25073 to 25822)

```
  1 atgacgcaaa gactgaagga caagcttgca gtaattaccg gcggtgccaa cggcatcggg
 61 cgggcaattg cggagcgatt tgcggtcgaa ggtgccgaca tcgcaatcgc ggatctggtg
121 ccggccccgg aagccgaggc agcaatcagg aacctcggtc ggcgcgttct gaccgtgaag
181 tgcgatgtct cgcaacctgg cgacgtagaa gcattcggaa agcaggtcat ctccacgttt
241 ggtcgctgcg acatcctcgt caacaacgcg ggaatttacc cgctgattcc ttttgacgag
301 ctgacctttg aacagtggaa gaaaacattc gagatcaacg tcgattcagg ttttcttatg
361 gcgaaggctt ttgtccccgg gatgaagagg aacgggtggg gacgcatcat caacctgact
421 tcgacgacat attggctaaa gatcgaggcg tatacccatt acatcagcac gaaagcggca
481 aacataggct ttaccgcgcg ccttgcctcg gacctgggga aggacggaat cactgttaac
541 gccatcgcgc cgagccttgt ccgcacggca acaaccgaag cttctgcatt gtccgcgatg
601 ttcgacgtgc tgccaaacat gcttcaggcg attccgcgtc ttcaggtgcc cctggatctg
661 acgggcgcag ctgcgttcct ggcttccgat gacgccagtt ttattacagg ccagacgctc
721 gcggttgatg gcggtatggt gagacactga
```

SEQ ID NO:2 Amino acid sequence of the phenylethanol dehydrogenase from *Azoarcus* sp EbN1 (GenBank protein ID CAD58337)

```
  1 MTQRLKDKLA VITGGANGIG RAIAERFAVE GADIAIADLV PAPEAEAAIR
 51 NLGRRVLTVK CDVSQPGDVE AFGKQVISTF GRCDILVNNA GIYPLIPFDE
101 LTFEQWKKTF EINVDSGFLM AKAFVPGMKR NGWGRIINLT STTYWLKIEA
151 YTHYISTKAA NIGFTRALAS DLGKDGITVN AIAPSLVRTA TTEASALSAM
201 FDVLPNMLQA IPRLQVPLDL TGAAAFLASD DASFITGQTL AVDGGMVRH
```

METHOD FOR PRODUCING L-PHENYLEPHRINE USING AN ALCOHOL DEHYDROGENASE OF *AROMATOLEUM AROMATICUM* EBN1 (*AZOARCUS* SP. EBN1)

RELATED APPLICATIONS

This application is a national stage application (under 35 U.S.C. §371) of PCT/EP2009/061974, filed Sep. 15, 2009, which claims benefit of European Application No. 08164488.2, filed Sep. 17, 2008.

The present invention relates to a multistage method of production of substituted, optically active alcohols, comprising an enzyme-catalyzed synthesis step, in particular catalyzed by an alcohol dehydrogenase. The method according to the invention is suitable in particular for the production of phenylephrine, i.e. 3-[(1R)-1-hydroxy-2-methylamino-ethyl]-phenol.

BACKGROUND OF THE INVENTION

Phenylephrine is a pharmacological active substance in the sympathomimetics group and possesses agonistic activity on the $\alpha_1$-adrenergic receptor. Apart from the missing 3-hydroxyl group it is structurally the same as adrenaline and mainly finds application as a local vasoconstrictor. As the active substance in nasal drops it therefore has a decongestant action on the mucosae. In eye drops it also has mydriatic action, and thus leads to dilation of the pupils.

The production of phenylephrine is already described in the literature. In addition to the numerous methods for production of the desired product as racemate and then transforming it to the product by cleavage with a suitable chiral auxiliary agent, the methods of stereoselective synthesis are to be regarded as preferable, as it is then possible to avoid the uneconomic destruction of the resultant 50% of incorrect enantiomer.

The methods of production of L-phenylephrine hydrochloride known from the prior art include the asymmetric hydrogenation of the prochiral N-benzy-N-methyl-2-amino-m-benzyloxyacetophenone hydrochloride according to Tetrahedron Letters 30 (1989), 367-370, or Chem. Pharm. Bull. 43 (5) (1995) 738-747.

Achiwa et al. describe in Tetrahedron Letters 30 (1989), 367-370 the asymmetric hydrogenation of 3-benzyloxy-2-(N-benzyl-N-methyl)-aminoacetophenone hydrochloride as substrate with hydrogen in the presence of [Ph(COD)Cl]$_2$/(2R,4R)-4-(dicyclohexylphosphino)-2-(diphenylphosphino-methyl)-N-methyl-aminopyrrolidine as catalyst. Immediately after filtration and concentration of the reaction mixture by evaporation, the benzyl nitrogen protective group is cleaved and phenylephrine is obtained as product. Along with the L-enantiomer, the D-enantiomer is produced as impurity in a proportion of at least 7.5% (85% ee). For the reaction, the catalyst must be used in a molar ratio of 1:2000 relative to the substrate. The drawback of this method is essentially that the L-phenylephrine obtained cannot be purified economically to a purity of at least 98% ee, which is required for use as a medicinal product.

In Chem. Pharm. Bull. 43 (5) (1995) 738-747, a molar ratio of substrate to catalyst of about 1000:1 is stated to be preferable for the asymmetric hydrogenation. However, despite the use of quite large amounts of catalyst in the asymmetric reaction step, the product cannot be produced in sufficient purity as L-enantiomer for pharmaceutical purposes without expensive purification procedures, but can only be obtained as a mixture with a relatively high proportion of D-enantiomer as impurity. The relatively long reaction time of the asymmetric hydrogenation step of approx. 20 hours also represents, for the production of L-phenylephrine on an industrial scale, a reaction step that is expensive and costly in terms of equipment, with a safety risk that cannot be ignored.

The method described in WO 00/43345 fulfills some of the stated conditions for an economically meaningful production of L-phenylephrine hydrochloride but here too the use of protective groups is still required, so that the method becomes less economical. Furthermore, even according to this method, in the stereoselective step the desired product is only obtained at 93% ee, so that once again it must be followed by expensive purification.

BRIEF DESCRIPTION OF THE INVENTION

The problem to be solved by the present invention is therefore to provide a novel method of production of optically active alcohols, such as L-phenylephrine, which can be carried out more economically in comparison with the prior art. In particular said improved method should not require the use of protective groups and should possess high stereoselectivity.

Surprisingly, the above problem could be solved by providing a method of production of substituted, optically active alcohols of formula IV

according to the appended patent claims.

On this basis, the present invention makes possible in particular a surprisingly advantageous method of production of the active substance phenylephrine (3-[(1R)-1-hydroxy-2-methylamino-ethyl]-phenol; 4). This preferred embodiment can be represented by the following reaction scheme:

Scheme 1:

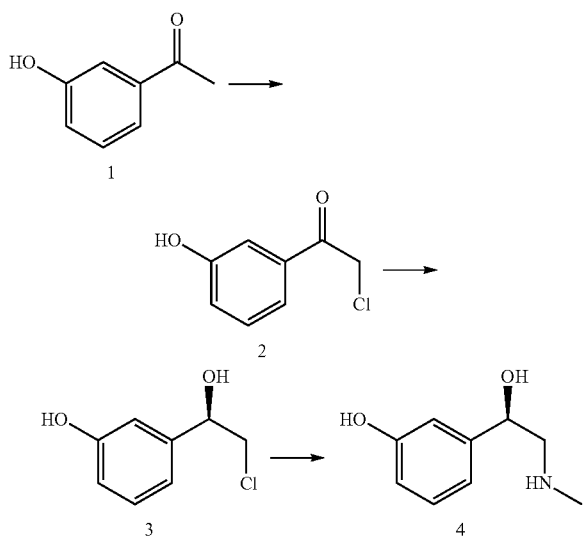

One of the two key steps in this is the selective side-chain chlorination of 3'-hydroxyacetophenone (3-HAP, 1) to 3'-hydroxy-2-chloroacetophenone (HCAP, 2).

The second key step relates to the enantioselective reduction of HCAP (2) to (R)-3-(2-chloro-1-hydroxyethyl)-phenol (HCPE, 3), in particular using an enzyme, namely an alcohol dehydrogenase (ADH).

The method provided according to the invention differs significantly in some essential points from the prior art discussed above.

Thus, the entire synthesis is achieved without the use of protective groups, so that the method is more economical compared with the prior art. This is surprising and unexpected, especially for the first stage.

The use of dehydrogenase as hydrogenation catalyst provides an economical route to (R)-3-(2-chloro-1-hydroxyethyl)-phenol (HCPE, 3) of high optical purity. No notable amounts of the unwanted enantiomer are formed (the % ee values for the desired enantiomer are in the range >98%, e.g. >99% up to about 100%, for example up to about 99.9%).

The reaction can (without being restricted to this) moreover be carried out in a two-phase system of organic solvent and water, which moreover allows more economical operation. Complete conversion of the ketone to the desired alcohol is then possible. Further processing of the mixture is especially favorable owing to its two-phase nature, because the product is separated from catalyst residues (protein) by extraction. Moreover, use of the organic phase lessens the exposure of the biocatalyst to the low-molecular, phenolic ketone, so that inactivation and/or inhibition of the catalyst is prevented.

DESCRIPTION OF THE DRAWING

FIG. 1 shows the nucleic acid sequence and amino acid sequence of phenyl-ethanol dehydrogenase from (*Azoarcus* sp) *Aromatoleum aromaticum* EbN1 (SEQ ID NO: 1 and 2 respectively).

DETAILED DESCRIPTION OF THE INVENTION

1. Preferred Embodiments

A first object of the invention relates to a method of production of substituted, optically active alcohols of formula IV

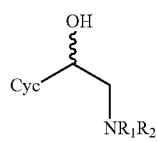

in which

Cyc stands for a mono- or polynuclear, in particular mononuclear, 4- to 7-membered, in particular 5- or 6-membered, saturated or unsaturated, in particular unsaturated, mainly aromatic, carbocyclic or heterocyclic, in particular carbocyclic, ring, which has at least one free hydroxyl group, and is optionally substituted one or more times, and in the case of a 6-membered ring the hydroxyl group(s) are in particular in the meta-position to the side chain of Cyc bearing amino groups; and $R_1$ and $R_2$ independently of one another stand for H or identical or different alkyl residues optionally substituted one or more times;

or of salts of this compound, e.g. salts of acid addition of in particular inorganic acids, such as HCl; in each case in stereoisomerically pure form, for example the (R) or (S) form, or as a mixture of stereoisomers, e.g. racemates, wherein a) a ketone of formula I

in which Cyc has the meanings stated above, is halogenated, such as in particular chlorinated, in the presence of an, in particular aliphatic, alcohol, and is reacted, especially with sulfuryl chloride, to a halogenated, in particular chlorinated, compound of formula II

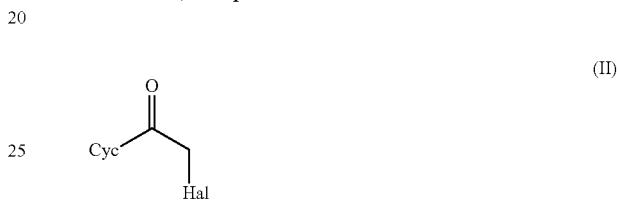

in which Cyc has the meanings stated above and Hal stands for a halogen atom, for example F, Br or in particular Cl;

b) the resultant compound of formula II, optionally after previous isolation or enrichment, is reduced enzymatically to the alcohol of formula III

in which Cyc and Hal have the meanings stated above; and c) the resultant alcohol of formula III, optionally after previous isolation or enrichment, is reacted with an amine of formula $HNR_1R_2$, in which $R_1$ and $R_2$ have the meanings stated above, to the compound of formula IV and optionally these are isolated from the reaction mixture, optionally in stereoisomerically pure form.

The ketones of the above formula I used for the synthesis are compounds that are known per se and can be obtained using generally known methods of organic Synthesis.

In particular, the reaction in stage a) takes place in the presence of 1 to 10, 2 to 8 or 3 to 5 molar equivalents of the aliphatic alcohol per mol of ketone of formula I.

Suitable aliphatic alcohols are in particular mono- or polyols with 1 to 6, in particular 1 to 4 carbon atoms and 1 to 5, in particular 1 to 3 hydroxyl groups, in particular monools with 1 to 4 carbon atoms, e.g. methanol, ethanol, n-propanol, n-butanol; or longer-chain monools, such as n-pentanol and n-hexanol, or polyols, such as propanediol, butane-1,4-diol, pentane-1,5-diol, hexane-1,6-diol or pentane-1,3,5-triol; and isomeric forms of said alcohols.

The chemical reaction in stage c) can in particular take place in solution in an open-chain or cyclic ether. Suitable ethers are in particular MTBE, methyl-THF, dioxane and in particular THF.

In particular, stage b) of the reaction according to the invention is catalyzed by at least one enzyme, selected from alcohol dehydrogenases (ADH) (E.C. 1.1.1.1).

The ADHs are for example selected from dehydrogenases from microorganisms of the genus *Aromatoleum* (*Azoarcus*), in particular from the bacterium *Aromatoleum aromaticum* EbN1.

For example, the enzyme for carrying out stage b) is selected from enzymes that have a polypeptide sequence that is selected from (i) SEQ ID NO: 2 or (ii) sequences in which up to 25%, for example 1 to 24%, 2 to 20%, 3 to 15% or 4 to 10%, of the amino acid residues are altered relative to SEQ ID NO: 1 by addition, deletion, insertion, substitution, inversion or a combination thereof, and/or that still have at least 50%, for example at least 60, 70, 80, 90, 95, 96, 97, 98, 99, 100 or more than 100%, e.g. 1 to 20 times, or 2 to 10 times or 3 to 5 times the activity of the enzymatic activity of an enzyme according to SEQ ID NO:2.

According to another embodiment the reaction in stage b) takes place with addition of reduction equivalents, in particular NADH or NADPH, and optionally with simultaneous or time-shifted regeneration of the reduction equivalents consumed in the reaction.

For this, the regeneration can take place enzymatically, electrochemically or electro-enzymatically in a manner known per se (*Biotechnology Progress*, 2005, 21, 1192; *Biocatalysis and Biotransformation*, 2004, 22, 89; *Angew. Chem. Int. Ed. Engl.*, 2001, 40, 169; *Biotechnol Bioeng*, 2006, 96, 18; *Biotechnol Adv.*, 2007, 25, 369; *Angew. Chem. Int. Ed. Engl*, 2008, 47, 2275; *Current Opinion in Biotechnology*, 2003, 14, 421; *Current Opinion in Biotechnology*, 2003, 14, 583). In particular the regeneration takes place enzymatically, and the regenerating enzyme is selected from ADH (EC.1.1.1.1) and dehydrogenases different from ADH, such as in particular glucose dehydrogenases (EC 1.1.1.47), formate dehydrogenases (EC 1.2.1.2 or EC 1.2.1.43), and phosphite dehydrogenases (EC 1.20.1.1) and preferably in the presence of a so-called "sacrificial alcohol", for example butan- or pentan-2-ol, which is consumed, i.e. oxidized, in the enzymatic regeneration of the reduction equivalents.

In particular, the reaction in stage b) can take place either in the presence of a microorganism, which expresses ADH naturally or recombinantly, or in the presence of a fraction containing ADH derived therefrom, i.e. obtained from the cells, or a cellular extract obtained from the cells, or in the presence of the pure or essentially pure enzyme. The enzymes used according to the invention (in pure form, in enriched form, or as enzyme-containing cellular extract) are moreover used in a manner known per se, dissolved, dispersed or immobilized on a support.

For example, the reaction in stage b) takes place in the presence of a microorganism that is selected from bacteria of the families Enterobacteriaceae, Pseudomonadaceae, Bacillaceae, Rhizobiaceae, Lactobacillaceae, Streptomycetaceae, Rhodococcaceae, Rhodocyclaceae and Nocardiaceae, or in the presence of a fraction or extract derived therefrom. Examples of suitable genera comprise in particular *Escherichia*, *Streptomyces*, *Corynebacterium* and *Bacillus*. Examples of suitable species are in particular *E. coli*.

In particular the microorganism can be a recombinant microorganism, which has been transformed with a nucleic acid construct, which encodes an ADH according to the above definition. Optionally the recombinant microorganism used can additionally express an exogenous or endogenous dehydrogenase, different from ADH, according to the above definition, to support the cofactor regeneration.

In another embodiment the reaction in stage b) can be carried out in a two-phase liquid reaction medium. For this, for example, an aqueous-organic reaction medium is used, with both the educt of formula II and the product of formula III being more soluble in the organic phase than in the aqueous phase, such as e.g. an aqueous-ethereal phase, or e.g. water/heptane and water/hexane phases.

Another object of the invention relates to a method of production of a compound of general formula II,

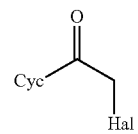

(II)

in which Cyc and Hal have the meanings stated above, wherein a ketone of formula I

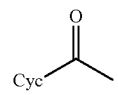

(I)

in which Cyc has the meanings stated above, is halogenated, in particular chlorinated, in particular is reacted in the presence of an aliphatic alcohol with a suitable halogenating agent, such as in particular sulfuryl chloride, to the halogenated, in particular chlorinated compound of formula II.

The reaction in stage a) takes place in particular in the presence of 1 to 10, for example 2 to 8 or 3 to 5, molar equivalents of alcohol per mol of ketone of formula I.

Another object of the invention relates to a method of production of a compound of formula III

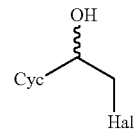

(III)

in which Cyc and Hal have the meanings stated above; wherein a compound of general formula II

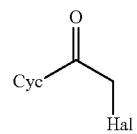

(II)

in which Cyc and Hal have the meanings stated above, is reduced enzymatically to the alcohol of formula III. During this, the enzymatic reaction is carried out as defined above.

According to the invention, Cyc stands in particular for a mononuclear, carbocyclic or heterocyclic 4-, 5- or 6-membered aromatic ring, bearing at least one HO— group, such as in particular for a 3-hydroxyphenyl residue. Hal stands in particular for a chlorine atom.

Another object of the invention relates to the use of an alcohol dehydrogenase according to the above definition or a microorganism producing this enzyme according to the above definition for the production of compounds of formulas III or IV, in particular for the production of (3-[(1R)-1-hydroxy-2-methylamino-ethyl]-phenol).

2. Definitions 2.1 General Terms

Unless stated otherwise, the following general meanings apply:

"Optically active" are, according to the invention, compounds with at least one center of asymmetry in the molecule.

A "free hydroxyl group" means, according to the invention, that it is not in derivatized form, e.g. as ester or ether group.

The term "stereoisomerically pure or enantiomerically pure products", such as (3-[(1R)-1-hydroxy-2-methylamino-ethyl]-phenol or (R)-3-(2-chloro-1-hydroxyethyl)-phenol, means, according to the invention, enantiomers that display enantiomeric enrichment. In particular, in the method according to the invention, enantiomeric purities of at least 90% ee, preferably of at least 95% ee, especially preferably of at least 98% ee, and quite especially preferably at least 99% ee or more, are attained.

The "enantiomeric purity" is defined with the parameter $ee \% = [X_A - X_B]/[X_A + X_B] * 100$, in which $X_A$ and $X_B$ stand for the mol fraction of enantiomers A and B.

A reaction takes place "enzymatically" either in the presence of pure enzymes, enriched enzymes or whole cells.

2.2 Special Chemical Terms

"Mono- or polynuclear" residues are residues that comprise one or more cyclic groups, and in the case of polynuclear residues said cyclic groups can be joined together directly or via usual bridging groups or can be condensed with one another.

"Carbocyclic" residues comprise exclusively ring carbon atoms; "heterocyclic" residues comprise in addition one or more, e.g. 1, 2 or 3, identical or different ring heteroatoms, such as N, O or S.

These carbocyclic or heterocyclic rings comprise in particular 3 to 12, preferably 4, 5 or 6 ring carbon atoms. As examples we may mention cyclopropyl, cyclobutyl, cyclopentyl, cyclohexyl, cycloheptyl, the singly or multiply unsaturated analogs thereof, such as cyclobutenyl, cyclopentenyl, cyclohexenyl, cycloheptenyl, cyclohexadienyl, cycloheptadienyl; and 5- to 7-membered saturated or singly or multiply unsaturated heterocyclic residues with 1 to 4 heteroatoms, which are selected from O, N and S, wherein the heterocycle can optionally have been condensed with another heterocycle or carbocycle. We may mention in particular heterocyclic residues derived from pyrrolidine, tetrahydrofuran, piperidine, morpholine, pyrrole, furan, thiophene, pyrazole, imidazole, oxazole, thiazole, pyridine, pyran, pyrimidine, pyridazine, pyrazine, coumarone, indole and quinoline.

Nonlimiting examples of suitable "substituents" are selected from halogen, OH, —SH, —$NO_2$, low-alkyl, low-alkenyl, low-alkoxy and aryl.

"Halogen" stands for fluorine, chlorine, bromine or iodine, in particular fluorine, bromine or chlorine.

"Low-alkyl" stands for linear or branched alkyl residues with 1 to 6 carbon atoms, such as methyl, ethyl, i- or n-propyl, n-, i-, sec- or tert.-butyl, n-pentyl or 2-methyl-butyl, n-hexyl, 2-methyl-pentyl, 3-methyl-pentyl, 2-ethyl-butyl.

"Low-alkenyl" stands for the singly or multiply, preferably singly or doubly unsaturated analogs of the aforementioned alkyl residues with 2 to 6 carbon atoms, the double bond being located in any position of the carbon chain.

"Low-alkoxy" stands for the oxygen-terminated analogs of the aforementioned alkyl residues.

"Aryl" stands for a mono- or polynuclear, preferably mono- or binuclear, optionally substituted aromatic residue, in particular for phenyl or for a naphthyl bound via any ring position, such as 1- or 2-naphthyl. These aryl residues can optionally bear 1 or 2 identical or different substituents, selected from halogen, low-alkyl, low-alkoxy according to the above definition or trifluoromethyl.

Examples of suitable Cyc residues are phenyl, naphthyl, 2-thienyl, 3-thienyl; 2-furanyl, 3-furanyl; 2-pyridyl, 3-pyridyl or 4-pyridyl; 2-thiazolyl, 4-thiazolyl or 5-thiazolyl; 4-methyl-2-thienyl, 3-ethyl-2-thienyl, 2-methyl-3-thienyl, 4-propyl-3-thienyl, 5-n-butyl-2-thienyl, 4-methyl-3-thienyl, 3-methyl-2-thienyl; 3-chloro-2-thienyl, 4-bromo-3-thienyl, 2-iodo-3-thienyl, 5-iodo-3-thienyl, 4-fluoro-2-thienyl, 2-bromo-3-thienyl, and 4-chloro-2-thienyl, which additionally bear at least one hydroxyl ring substituent.

3. Special Embodiments of the Method According to the Invention

Further embodiments of the invention are explained below, referring to the multistage reaction presented in the aforementioned scheme 1. On this basis, modifications of this concretely described method are within the ability of a person skilled in the art.

3.1 Selective Side-Chain Chlorination of 3'-hydroxyacetophenone

The principle of using sulfuryl chloride for the α-chlorination of ketones is known per se and is described for example in D. P. Wyman et al., J. Organic. Chem. Vol. 29, 1964, pages 1956 to 1960.

U.S. Pat. No. 4,310,702 and D. Masilamani et al., J. Organic. Chem., Vol. 46, 1981, pages 4486 to 4489 report that the use of sulfuryl chloride for the chlorination of ketones generally leads to a mixture of singly and multiply chlorinated ketones and therefore to undesirable by-products. To solve the problem, the publications teach the use of alcohols or ethers as moderator. Furthermore, this publication teaches the reaction of phenol with sulfuryl chloride, which leads first to the corresponding sulfonic acid ester and then to various chlorophenols. U.S. Pat. No. 5,710,341, which relates to the production of α-chloroalkylaryl ketones by chlorination of the corresponding ketone with sulfuryl chloride, also teaches the use of aliphatic alcohols to increase the selectivity for the desired product, i.e. the mono-α-chlorinated ketone.

Now it was found, surprisingly, that under the conditions taught in U.S. Pat. No. 5,710,341, the reaction of 3-hydroxy-acetophenone which is used advantageously for the synthesis of phenylephrine, a chlorination leads almost exclusively to the corresponding α-chloroalkylaryl ketones. To control the selectivity, 1-10 equivalents of an alcohol ($C_1$-$C_{10}$) are added to the reaction mixture; especially preferably, between 3 and 5 equivalents of the alcohol are used. Furthermore, the reaction is carried out in a solvent that is inert under the reaction conditions, such as for example aromatics, ethers, esters and halogenated solvents, which are immiscible with water. Preferably it is carried out in esters and halogenated solvents, especially preferably in ethyl acetate or dichloromethane.

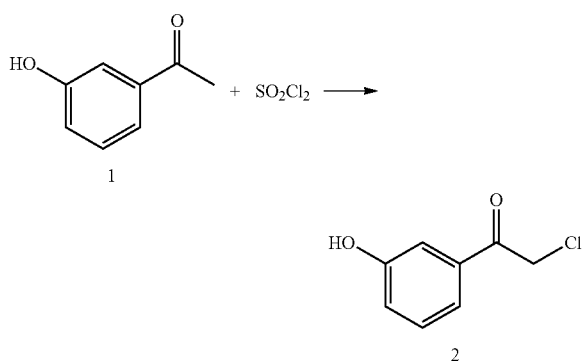

This is surprising to a person skilled in the art, as reaction of the phenolic functionality present in the molecule would be expected, analogously to the manner taught by D. Masilamani, to lead to formation of the corresponding chlorophenols. Advantageously, the reaction can be carried out without the use of a protective group.

3.2 Enantioselective Hydrogenation of 3'-hydroxy-2-chloroacetophenone

The reduction of 2 is catalyzed by an enzyme. It is dehydrogenase EbN1 from (*Azoarcus* sp.) *Aromatoleum aromaticum* EbN1, which in the particular case is prepared recombinantly in *Escherichia coli*.

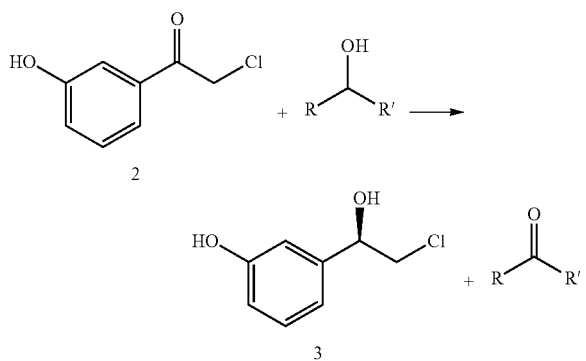

It is known that dehydrogenases are suitable as biocatalysts for the production of optically active hydroxy compounds. They are well-characterized biocatalysts, which are already used in a number of technical processes (*Angew. Chem. Int. Ed.*, 2004, 43, 788; *Tetrahedron*, 2004, 60, 633; *Chiral catalysis—asymmetric hydrogenation supplement to Chemistry Today*, 2004, 22, 26; *Current Opinion in Chemical. Biology*, 2004, 8, 120; *Organic Process Research & Development*, 2002, 6, 558; *Tetrahedron: Asymmetry*, 2003, 14, 2659; *Chiral catalysis—asymmetric hydrogenation supplement to Chemistry Today*, 2004, 22, 43).

Dehydrogenases convert ketones or aldehydes to the corresponding secondary or primary alcohols; in principle the reaction is reversible. They catalyze the enantioselective hydride transfer to the prochiral carbon atom of the carbonyl compound.

The hydride ions are [lacuna] by so-called cofactors, e.g. NADPH or NADH (reduced nicotinamide-adenine dinucleotide phosphate or reduced nicotinamide-adenine dinucleotide). As these are very expensive compounds, they are only added in catalytic amounts to the reaction mixture. The reduced cofactors are regenerated during the reaction by a second redox reaction, occurring simultaneously. Depending on the thermodynamic and kinetic conditions of the overall reaction, low-cost secondary alcohols (so-called "sacrificial alcohols") such as isopropanol can occur as final hydride donor of the reaction, as is known from the Meerwein-Ponndorf-Verley reaction. Often ketone reduction and sacrificial alcohol oxidation can be carried out by the same biocatalyst (substrate coupling).

Alternatively a second catalyst can be used for regenerating the spent cofactors. Known examples are formate dehydrogenase, glucose dehydrogenase or phosphite dehydrogenase, which from the oxidation of formate, glucose or phosphite transfer hydride ions from NAD or NADP. (*Biocatalysis and Biotransformation*, 2004, 22, 89; *Applied Microbiology and Biotechnology*, 1997, 48, 699; *Bioscience Biotechnology and Biochemistry*, 1998, 62, 167; *Methods Enzymol.*, 1987, 136, 9; *Ann. N.Y. Acad. Sci.*, 1984, 434, 91; *FEBS Journal*, 2005, 272, 3816; *Applied Microbiology and Biotechnology*, 2003, 61, 133).

The reduction equivalents of the reaction examined here originate either from isopropanol (or another secondary so-called "sacrificial alcohol") which is oxidized to acetone, or from glucose, which is oxidized in a parallel reaction to gluconolactone. Whereas the oxidation of many sacrificial alcohols by the same enzyme that also performs the reduction of 2 to R-3 is possible, for the oxidation of glucose it is necessary to add glucose dehydrogenase as second enzyme.

Alternatively, instead of glucose dehydrogenase it is also possible to use another regeneration system, for example phosphite dehydrogenase (*Biotechnol Bioeng*, 2006, 96, 18) or electrochemical cofactor regeneration (*Angew. Chem. Int. Ed Engl.*, 2001, 40, 169), (*Angewandte Chemie Int. Ed. Engl.*, 1999, 29, 388).

Suitable biocatalysts for the production of R-3 have already been described in the following patent applications of BASF SE: (DE 2004022686, EP 2005004872, WO 2005108590) or (EP 06123814, WO2008055988 A3).

3.2 Production of L-Phenylephrine

This novel method of production of L-phenylephrine and its salts concludes with reaction of component 3, obtained after reduction, with methylamine to the desired product.

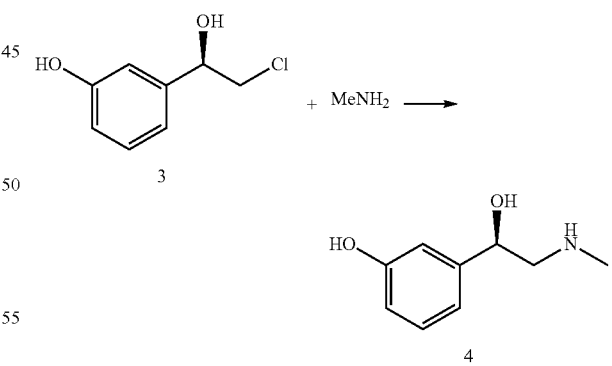

This is achieved in many various solvents that are inert in the reaction conditions, such as e.g. water, alcohols or ethers. The ethers are especially preferred, in which the starting material 3 dissolves to a great extent, for operation in economically meaningful concentrations. The use of THF is especially preferred. After the reaction, L-phenylephrine can be obtained as base and in the form of its salts, for example but not exclusively according to the method taught in WO 00/43345.

4. Further Embodiments of the Invention

4.1 Alcohol Dehydrogenases

The enzyme used according to the invention is in particular selected from alcohol dehydrogenases (E.C. 1.1.1.1).

Without being restricted to this, such enzymes are preferably obtained from microorganisms of the genera *Aromatoleum* (sometimes also designated as *Azoarcus*), e.g. *Aromatoleum aromaticum*, especially strain EbN1.

Preferred enzymes with ADH activity comprise an amino acid sequence according to SEQ ID NO: 2.

"Functional equivalents" of the concretely disclosed ADHs and the use thereof in the method according to the invention are also included according to the invention.

"Functional equivalents" or analogs of the concretely disclosed enzymes are, within the scope of the present invention, various polypeptides, which moreover possess the desired biological activity, for example substrate specificity. For example, "functional equivalents" is understood to include enzymes that reduce 3'-hydroxy-2-chloroacetophenone 2 to the corresponding R-alcohol (R)-3-(2-chloro-1-hydroxyethyl)phenol 3 and that have at least 20%, preferably 50%, especially preferably 75%, quite especially preferably 90% of the activity of an enzyme comprising one of the amino acid sequence listed under SEQ ID NO:2.

"Functional equivalents" are understood according to the invention to include in particular mutants, which in at least one sequence position of the aforementioned amino acid sequences have an amino acid other than that concretely stated but nevertheless possess one of the aforementioned biological activities. "Functional equivalents" therefore comprise the mutants obtainable by one or more amino acid additions, substitutions, deletions and/or inversions, wherein the stated changes can occur in any sequence position, provided they result in a mutant with the property profile according to the invention. Functional equivalence is in particular also achieved when the reactivity patterns between mutant and unaltered polypeptide coincide qualitatively, i.e. for example identical substrates are converted at a different velocity.

"Functional equivalents" in the above sense are also "precursors" of the polypeptides described and "functional derivatives" and "salts" of the polypeptides.

"Precursors" are natural or synthetic precursors of the polypeptides with or without the desired biological activity.

The term "salts" means salts of carboxyl groups as well as salts of acid addition of amino groups of the protein molecules according to the invention. Salts of carboxyl groups can be prepared in a manner known per se and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid are also covered by the invention.

"Functional derivatives" of polypeptides according to the invention can also be prepared on functional amino acid side groups or on their N- or C-terminal end by known techniques. Such derivatives comprise for example aliphatic esters of carboxylic acid groups, amides of carboxylic acid groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups.

"Functional equivalents" naturally also comprise polypeptides that are obtainable from other organisms, and naturally occurring variants. For example, using sequence comparison it is possible to determine domains of homologous sequence regions and determine equivalent enzymes on the basis of the concrete instructions of the invention.

"Functional equivalents" also comprise fragments, preferably individual domains or sequence motifs, of the polypeptides according to the invention, which e.g. have the desired biological function.

"Functional equivalents" are moreover fusion proteins, which have one of the aforementioned polypeptide sequences or functional equivalents derived therefrom and at least one other, functionally different, heterologous sequence in functional N- or C-terminal linkage (i.e. without mutual substantial functional impairment of the fusion protein parts). Non-limiting examples of said heterologous sequences are e.g. signal peptides or enzymes.

"Functional equivalents" also included according to the invention are homologs of the concretely disclosed proteins. These possess at least 60%, preferably at least 75%, especially at least 85%, e.g. 90, 91, 92, 93, 94, 95, 96, 97, 98 or 99%, homology to one of the concretely disclosed amino acid sequences. A percentage homology of a homologous polypeptide according to the invention means in particular the percentage identity of the amino acid residues referred to the total length of one of the amino acid sequences described concretely herein.

"Identity" between two sequences means in particular the identity of the residues over the respective total sequence length, in particular the identity that is calculated by comparison using the Vector NTI Suite 7.1 (Vector NTI Advance 10.3.0, Invitrogen Corp.) (or software from the company Informax (USA)) using the Clustal Method (Higgins D G, Sharp P M. Fast and sensitive multiple sequence alignments on a microcomputer. Comput Appl. Biosci. 1989 April; 5(2): 151-1) on setting the following parameters:

| Multiple alignment parameter: | |
| --- | --- |
| Gap opening penalty | 10 |
| Gap extension penalty | 0.05 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | off |
| K-tuple size | 1 |
| Gap penalty | 3 |
| Window size | 5 |
| Number of best diagonals | 5 |

In the case of a possible protein glycosylation "functional equivalents" according to the invention comprise proteins of the type designated above in deglycosylated or glycosylated form and modified forms obtainable by changing the glycosylation pattern.

Homologs of the proteins or polypeptides according to the invention can be produced by mutagenesis, e.g. by point mutation or shortening of the protein.

Homologs of the proteins according to the invention can be identified by screening combinatorial banks of mutants, e.g. shortened mutants. For example, a varied bank of protein variants can be produced by combinatorial mutagenesis at the nucleic acid level, e.g. by enzymatic ligation of a mixture of synthetic oligonucleotides. There are a great many methods that can be used for the production of banks of potential homologs from a degenerated oligonucleotide sequence. The chemical synthesis of a degenerated gene sequence can be carried out in an automatic DNA synthesizer, and the synthetic gene can then be ligated into a suitable expression vector. Use of a degenerated set of genes makes it possible to prepare all sequences in one mixture, which encode the desired set of potential protein sequences. Methods for the synthesis of degenerated oligonucleotides are known by a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques are known in the prior art for the screening of gene products in combinatorial banks, which were produced by point mutations or shortening, and for the screening of cDNA banks for gene products with a selected property. These techniques can be adapted for the rapid screening of the gene banks that have been produced by combinatorial mutagenesis of homologs according to the invention. The techniques used most often for screening large gene banks, which form the basis of high-throughput analysis, comprise the cloning of the gene bank into replicatable expression vectors, transformation of suitable cells with the resultant vector bank and expression of the combinatorial genes under conditions in which detection of the desired activity facilitates the isolation of the vector that encodes the gene whose product was detected. Recursive ensemble mutagenesis (REM), a technique that increases the frequency of functional mutants in the banks, can be used in combination with the screening tests for identifying homologs (Arkin and Yourvan (1992) PNAS 89:7811-7815; Delgrave et al. (1993) Protein Engineering 6(3):327-331).

4.2 Coding Nucleic Acid Sequences

The terms "express" or "overexpression" describe, in the context of the invention, the production or increasing of the intracellular activity of one or more enzymes in a microorganism, which are encoded by the corresponding DNA. For this it is possible for example to insert a gene in an organism, replace an existing gene with another gene, increase the copy number of the gene or genes, use a strong promoter or use a gene that codes for a corresponding enzyme with high activity, and these measures can optionally be combined.

The invention relates in particular to nucleic acid sequences that code for an enzyme with ADH activity. Nucleic acid sequences comprising a sequence according to SEQ ID NO:1; or nucleic acid sequences derived from the amino acid sequences according to SEQ ID NO: 2, are preferred.

All nucleic acid sequences mentioned herein (single- and double-stranded DNA and RNA sequences, e.g. cDNA and mRNA) can be produced in a manner known per se by chemical synthesis from the nucleotide building blocks, for example by fragment condensation of individual overlapping, complementary nucleic acid building blocks of the double helix. The chemical synthesis of oligonucleotides can for example be carried out, in a known manner, according to the phosphoamidite method (Voet, Voet, 2nd edition, Wiley Press New York, pages 896-897). The addition of synthetic oligonucleotides and filling of gaps using the Klenow fragment of DNA polymerase and ligation reactions and general cloning methods are described in Sambrook et al. (1989), Molecular Cloning: A laboratory manual, Cold Spring Harbor Laboratory Press.

The invention also relates to nucleic acid sequences (single- and double-stranded DNA and RNA sequences, e.g. cDNA and mRNA) coding for one of the above polypeptides and functional equivalents thereof, which can be obtained e.g. using artificial nucleotide analogs.

The invention relates both to isolated nucleic acid molecules, which code for polypeptides or proteins according to the invention or biologically active segments thereof, and nucleic acid fragments, which can be used e.g. for use as hybridization probes or primers for the identification or amplification of coding nucleic acids according to the invention.

The nucleic acid molecules according to the invention can in addition contain untranslated sequences from the 3'- and/or 5'-end of the coding region of the gene.

The invention further comprises the nucleic acid molecules complementary to the concretely described nucleotide sequences or a segment thereof.

The nucleotide sequences according to the invention make possible the production of probes and primers that can be used for the identification and/or cloning of homologous sequences in other cell types and organisms. Said probes or primers usually comprise a nucleotide sequence region that hybridizes under "stringent" conditions (see below) to at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be essentially free from other cellular material or culture medium, when it is produced by recombinant techniques, or free from chemical precursors or other chemicals, when it is synthesized chemically.

A nucleic acid molecule according to the invention can be isolated by standard techniques of molecular biology and the sequence information provided according to the invention. For example, cDNA can be isolated from a suitable cDNA bank, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd ed., Cold Spring Harbor Laboratory, Cold Spring Harbor Laboratory Press, Cold Spring Harbor, N.Y., 1989). Moreover, a nucleic acid molecule, comprising one of the disclosed sequences or a segment thereof, can be isolated by a polymerase chain reaction, using the oligonucleotide primers that were prepared on the basis of this sequence. The nucleic acid thus amplified can be cloned into a suitable vector and can be characterized by DNA sequence analysis. The oligonucleotides according to the invention can moreover be produced by standard methods of synthesis, e.g. with an automatic DNA synthesizer.

Nucleic acid sequences according to the invention, such as SEQ ID NO: 1 or derivatives thereof, homologs or parts of these sequences, can be isolated for example with usual hybridization methods or the PCR technique from suitable microorganisms, e.g. via genomic or cDNA banks. These DNA sequences hybridize in standard conditions to the sequences according to the invention. Advantageously, short oligonucleotides are used for the hybridization. However, longer fragments of the nucleic acids according to the invention or the complete sequences can be used for the hybridization. These standard conditions are varied depending on the nucleic acid used (oligonucleotide, longer fragment or complete sequence) or depending on which type of nucleic acid DNA or RNA are used for the hybridization. For instance, the melting points for DNA:DNA hybrids are approx. 10° C. lower than those of DNA:RNA hybrids of the same length.

"Standard conditions" are to be understood, for example depending on the nucleic acid, as temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide such as for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for the hybridization are examples of calculated melting point values for a nucleic acid with a length of approx. 100 nucleotides and a G+C content of 50% in the absence of formamide. The experimental conditions for DNA hybridization are described in relevant textbooks of genetics, for example Sambrook et al., "Molecular Cloning", Cold Spring Harbor Laboratory, 1989, and can be calculated using formulas known by a person skilled in the art for example in relation to the length of the nucleic acids, the type of hybrids or the G+C content. A person skilled in the art can find further information on hybridization in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The invention also relates to derivatives of the concretely disclosed or derivable nucleic acid sequences.

Thus, other nucleic acid sequences according to the invention can be derived e.g. from SEQ ID NO:1 and can differ from it by addition, substitution, insertion or deletion of individual or several nucleotides, but still code for polypeptides with the desired property profile.

Nucleic acid sequences comprising so-called silent mutations or that are altered corresponding to the codon usage once special origin or host organism, in comparison with a concretely stated sequence, as well as naturally occurring variants, e.g. splicing variants or allelic variants, thereof, are also included according to the invention.

It also relates to sequences obtainable by conservative nucleotide substitutions (i.e. the amino acid in question is replaced with an amino acid of the same charge, size, polarity and/or solubility).

The invention also relates to molecules derived by sequence polymorphisms from the concretely disclosed nucleic acids. These genetic polymorphisms can exist between individuals within a population owing to natural variation. These natural variations usually bring about a variance of 1 to 5% in the nucleotide sequence of a gene.

"Derivatives" of the nucleic acid sequence according to the invention with the sequence SEQ ID NO: 1 are for example to be understood as allelic variants, which have at least 40% homology at the derived amino acid level, preferably at least 60% homology, quite especially preferably at least 80% homology over the entire sequence region (with respect to homology at the amino acid level, reference should be made to the above statements regarding the polypeptides). Over partial regions of the sequences the homologies can advantageously be higher.

Furthermore, "derivatives" are also to be understood as homologs of the nucleic acid sequences according to the invention, in particular of SEQ ID NO: 1, for example fungal or bacterial homologs, shortened sequences, single-stranded DNA or RNA of the coding and noncoding DNA sequence. For example, homologs to SEQ ID NO: 1 at DNA level possessed a homology of at least 40%, preferably of at least 60%, especially preferably of at least 70%, quite especially preferably of at least 80% over the entire DNA region shown in SEQ ID NO: 1.

Moreover, "derivatives" are to be understood for example as fusions with promoters. The promoters, which precede the stated nucleotide sequences, can be altered by one or more nucleotide exchanges, insertions, inversions and/or deletions, without the functionality and efficacy of the promoters being impaired. Moreover, the efficacy of the promoters can be increased by altering their sequence or they can be replaced completely with more effective promoters even from organisms of different species.

"Derivatives" are also to be understood as variants whose nucleotide sequences have been altered in the region of −1 to −1000 bases upstream in front of the start codon or 0 to 1000 bases downstream after the stop codon, so that gene expression and/or protein expression is altered, preferably increased.

Furthermore, the invention also comprises nucleic acid sequences that hybridize to the aforementioned coding sequences under "stringent conditions". These polynucleotides can be found by examining genomic or cDNA banks and optionally amplified from them with suitable primers by PCR and then isolated for example with suitable probes. Furthermore, polynucleotides according to the invention can also be synthesized chemically. This property is to be understood as the capacity of a poly- or oligonucleotide to bind in stringent conditions to an almost complementary sequence, whereas in these conditions nonspecific bindings between noncomplementary partners do not occur. For this, the sequences should be complementary to 70-100%, preferably to 90-100%. The property of complementary sequences to be able to bind specifically to one another is utilized for example in the Northern or Southern blot technique or in primer binding in PCR or RT-PCR. Usually oligonucleotides are used for this starting from a length of 30 base pairs. "Stringent conditions" are to be understood, for example in the Northern blot technique, as the use of a washing solution heated to 50-70° C., preferably 60-65° C., for example 0.1×SSC buffer with 0.1% SDS (20×SSC: 3M NaCl, 0.3M Na-citrate, pH 7.0) for the elution of nonspecifically hybridized cDNA probes or oligonucleotides. As mentioned above, only nucleic acids that are complementary to a high degree remain bound to one another. The setting of stringent conditions is known by a person skilled in the art and is described for example in Ausubel et al., Current Protocols in Molecular Biology, John Wiley & Sons, N.Y. (1989), 6.3.1-6.3.6.

4.3 Constructs Used According to the Invention

According to the invention, in addition expression constructs are used, containing under the genetic control of regulatory nucleic acid sequences, a nucleic acid sequence coding for an enzyme according to the invention; and vectors, comprising at least one of these expression constructs.

Preferably said constructs according to the invention comprise a promoter 5'-upstream of the respective coding sequence and a terminator sequence 3'-downstream and optionally other usual regulatory elements, in each case operatively linked to the coding sequence.

"Operative linkage" is understood as the sequential arrangement of promoter, coding sequence, terminator and optionally further regulatory elements in such a way that each of the regulatory elements can fulfill its function in the expression of the coding sequence as required. Examples of operatively linkable sequences are targeting sequences and enhancers, polyadenylation signals and the like. Further regulatory elements comprise selectable markers, amplification signals, replication origins and the like. Suitable regulatory sequences are described for example in Goeddel, Gene Expression Technology: Methods in Enzymology 185, Academic Press, San Diego, Calif. (1990).

A nucleic acid construct used according to the invention is to be understood in particular as the ADH with sequence SEQ ID NO: 1 and the derivatives and homologs thereof and the nucleic acid sequences derivable from SEQ ID NO: 1, which have been linked operatively or functionally to one or more regulatory signals advantageously for controlling, e.g. increasing, gene expression.

In addition to these regulatory sequences, the natural regulation of these sequences before the actual structural genes can still be present and optionally can have been genetically altered, so that the natural regulation has been switched off and expression of the genes has been increased. The nucleic acid construct can, however, also have been constructed more simply, i.e. no additional regulatory signals have been inserted before the coding sequence (e.g. SEQ ID NO: 1 or its homologs) and the natural promoter with its regulation has not been removed. Instead, the natural regulatory sequence is mutated so that regulation no longer takes place and gene expression is increased.

A preferred nucleic acid construct advantageously also contains one or more of the previously mentioned "enhancer" sequences, functionally linked to the promoter, which make increased expression of the nucleic acid sequence possible. Also at the 3'-end of the DNA sequences, additional advantageous sequences can be inserted, such as other regulatory elements or terminators. The nucleic acids according to the invention can be contained in the construct in one or more copies. The construct can also contain other markers, such as antibiotic resistances or auxotrophy-complementing genes, optionally for selection on the construct.

Advantageous regulatory sequences for the method according to the invention are contained for example in promoters such as cos-, tac-, trp-, tet-, trp-tet-, lpp-, lac-, lpp-lac-, lacI$^{q}$-, T7-, T5-, T3-, gal-, trc-, ara-, rhaP (RhaP$_{BAD}$)SP6-, lambda-P$_R$- or in the lambda-P$_L$-promoter, which advantageously find application in Gram-negative bacteria. Other advantageous regulatory sequences are contained for example in the Gram-positive promoters amy and SPO2, in the yeast or fungal promoters ADC1, MFalpha, AC, P-60, CYC1, GAPDH, TEF, rp28, ADH. In this connection, the promoters of pyruvate decarboxylase and methanol oxidase, for example from Hansenula, are also advantageous. Artificial promoters can also be used for regulation.

For expression, the nucleic acid construct is inserted in a host organism advantageously into a vector, for example a plasmid or a phage, which permits optimal expression of the genes in the host. As well as plasmids and phages, vectors are to be understood as any other vectors known by a person skilled in the art, for example viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent another embodiment of the invention. Suitable plasmids are for example in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, gt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^{+}$, pBIN19, pAK2004 or pDH51. The aforementioned plasmids represent a small selection of the possible plasmids. Further plasmids are certainly known by a person skilled in the art and will be found for example in the book Cloning Vectors (Eds. Pouwels P. H. et al. Elsevier, Amsterdam-New York-Oxford, 1985, ISBN 0 444 904018).

Advantageously the nucleic acid construct contains for expression of the other genes present, additionally 3'- and/or 5'-terminal regulatory sequences for increasing expression, which are selected for optimal expression depending on the selected host organism and gene or genes.

These regulatory sequences should make possible the targeted expression of the genes and protein expression. This can mean for example, depending on the host organism, that the gene is only expressed or overexpressed after induction, or that it is expressed and/or overexpressed immediately.

The regulatory sequences or factors can then preferably have a positive effect on and therefore increase expression of the inserted genes. Thus, intensification of the regulatory elements can take place advantageously at the transcription level, using strong transcription signals such as promoters and/or enhancers. In addition, however, intensification of translation is also possible, so that for example the stability of the mRNA is improved.

In another embodiment of the vector, the vector containing the nucleic acid construct according to the invention or the nucleic acid according to the invention can also advantageously be inserted in the form of a linear DNA into the microorganisms and be integrated via heterologous or homologous recombination into the genome of the host organism. This linear DNA can consist of a linearized vector such as a plasmid or only the nucleic acid construct or the nucleic acid according to the invention.

For optimal expression of heterologous genes in organisms it is advantageous to alter the nucleic acid sequences in accordance with the specific codon usage in the organism. The codon usage can easily be determined on the basis of computer evaluations of other, known genes of the organism in question.

An expression cassette according to the invention is prepared by fusion of a suitable promoter with a suitable coding nucleotide sequence and a terminator or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector, which permits optimal expression of the genes in the host. Vectors are certainly known by a person skilled in the art and will be found for example in "Cloning Vectors" (Pouwels P. H. et al., Eds., Elsevier, Amsterdam-New York-Oxford, 1985).

4.4 Hosts that can be Used According to the Invention

By means of the vectors according to the invention, recombinant microorganisms can be produced that have for example been transformed with at least one vector according to the invention and can be used for production of the polypeptides used according to the invention or for carrying out the enzymatic reaction according to the invention.

Advantageously, the recombinant constructs according to the invention, described above, are inserted into a suitable host system and expressed. Preferably, common cloning and transfection methods that are known by a person skilled in the art, for example co-precipitation, protoplast fusion, electroporation, retroviral transfection and the like, are used for expressing the stated nucleic acids in the respective expression system. Suitable systems are described for example in Current Protocols in Molecular Biology, F. Ausubel et al., Eds., Wiley Interscience, New York 1997, or Sambrook et al. Molecular Cloning: A Laboratory Manual. 2nd ed., Cold Spring Harbor Laboratory, Cold Spring Harbor Laboratory Press, Cold Spring Harbor, N.Y., 1989.

Homologously recombined microorganisms can also be produced according to the invention. For this, a vector is produced that contains at least one segment of a gene or a coding sequence according to the invention, in which optionally at least one amino acid deletion, addition or substitution has been incorporated, in order to alter the sequence according to the invention, e.g. disrupt it functionally ("knockout" vector). The sequence incorporated can for example also be a homolog from a related microorganism or can be derived from a mammalian, yeast or insect source. The vector used for the homologous recombination can alternatively be designed so that during homologous recombination the endogenous gene is mutated or altered in some other way, but still encodes the functional protein (e.g. the regulatory region located upstream can be altered in such a way that the expression of the endogenous protein is altered as a result). The altered segment of the gene according to the invention is in the homologous recombination vector. The construction of suitable vectors for homologous recombination is described for example in Thomas, K. R. and Capecchi, M. R. (1987) Cell 51:503.

In principle, all prokaryotic or eukaryotic organisms can be considered as recombinant host organisms for the nucleic acid according to the invention or the nucleic acid construct. Advantageously, microorganisms such as bacteria, fungi or yeasts are used as host organisms. Advantageously, Gram-positive or Gram-negative bacteria are used, preferably bacteria in the families Enterobacteriaceae, Pseudomonadaceae, Rhizobiaceae, Streptomycetaceae, Bacillaceae or Nocardiaceae, especially preferably bacteria of the genera *Escherichia, Pseudomonas, Streptomyces, Nocardia, Burkholderia, Salmonella, Agrobacterium, Bacillus* or *Rhodococcus*. The genus and species *Escherichia coli* is quite especially preferred. Other advantageous bacteria can be found, moreover, in the group of the alpha-proteobacteria, beta-proteobacteria or gamma-proteobacteria.

The host organism or host organisms according to the invention then preferably contain at least one of the nucleic acid sequences, nucleic acid constructs or vectors, which code for an ADH enzyme, described in this invention.

The organisms used in the method according to the invention are grown or cultured in a manner known by a person skilled in the art, depending on the host organism. Microorganisms are as a rule grown in a liquid medium, which contains a carbon source generally in the form of sugars, a nitrogen source generally in the form of organic nitrogen sources such as yeast extract or salts such as ammonium sulfate, trace elements such as iron, manganese, and magnesium salts and optionally vitamins, at temperatures between 0° C. and 100° C., preferably between 10° C. and 60° C. under oxygen aeration. The pH of the liquid medium can be maintained at a fixed value, i.e. regulated or not during the culture. Culture can be batchwise, semi-batchwise or continuous. Nutrients can be provided at the start of fermentation or more can be fed in semicontinuously or continuously.

The ketone to be converted can be added to the culture directly or advantageously after culture.

The enzymes can either be isolated from the organisms or can be used as raw extract for the reaction.

The host organisms contain e.g. 1 U/l enzyme activity, for instance ADH activity, preferably 100 U/l, especially preferably more than 1000 U/l.

4.5 Recombinant Production of Enzymes:

The enzymes used according to the invention can also be obtained by recombinant production, in which a microorganism producing this enzyme is cultivated, optionally expression of the polypeptides is induced and the latter are isolated from the culture. The polypeptides can also be produced on an industrial scale in this way, if desired.

The recombinant microorganism can be cultivated and fermented by known methods. Bacteria can be grown for example in TB or LB medium and at a temperature of 20 to 40° C. and a pH value from 6 to 9. Suitable culture conditions are described in detail for example in T. Maniatis, E. F. Fritsch and J. Sambrook, Molecular Cloning: A Laboratory Manual, Cold Spring Harbor Laboratory, Cold Spring Harbor, N.Y. (1989).

Then, if the polypeptides are not secreted in the culture medium, the cells are disrupted and the product is obtained from the lysate by known methods of protein isolation. The cells can optionally be disrupted by high-frequency ultrasound, by high pressure, e.g. in a French pressure cell, by osmolysis, by the action of detergents, lytic enzymes or organic solvents, by homogenizers or by a combination of several of the aforementioned methods.

Purification of the polypeptides can be effected with known chromatographic methods, such as molecular-sieve chromatography (gel filtration), such as Q-sepharose chromatography, ion-exchange chromatography and hydrophobic chromatography, and with other usual methods such as ultrafiltration, crystallization, salting-out, dialysis and native gel electrophoresis. Suitable methods are described for example in Cooper, F. G., Biochemische Arbeitsmethoden [biochemical procedures], Verlag Walter de Gruyter, Berlin, New York or in Scopes, R., Protein Purification, Springer Verlag, New York, Heidelberg, Berlin.

It may be advantageous, for isolation of the recombinant protein, to use vector systems or oligonucleotides that lengthen the cDNA by defined nucleotide sequences and therefore code for altered polypeptides or fusion proteins, which serve e.g. for easier purification. Suitable modifications of this kind are for example so-called "tags" that function as anchors, e.g. the modification known as a hexa-histidine anchor or epitopes that can be recognized as antigens by antibodies (described for example in Harlow, E. and Lane, D., 1988, Antibodies: A Laboratory Manual. Cold Spring Harbor (N.Y.) Press). These anchors can serve for securing the proteins on a solid support, e.g. a polymer matrix, which can for example be used as the packing in a chromatography column, or can be used on a microtiter plate or on some other support.

At the same time, these anchors can also be used for recognition of the proteins. For recognition of the proteins it is moreover possible to employ the usual markers, such as fluorescent dyes, enzyme markers, which after reaction with a substrate form a detectable reaction product, or radioactive markers, alone or in combination with the anchors for derivatization of the proteins.

4.6 Execution of Process Step b) According to the Invention for the Production of Optically Active Alcohols The enzymes used can be used in the process step according to the invention as free or immobilized enzymes.

The process step according to the invention is advantageously carried out at a temperature between 0° C. and 60° C., preferably between 10° C. and 40° C., especially preferably between 15° C. and 35° C.

The pH value during the process step according to the invention is advantageously maintained between pH 4 and 12, preferably between pH 4.5 and 9, especially preferably between pH 5 and 8.

For the method according to the invention it is possible to use growing cells, which contain the nucleic acids, nucleic acid constructs or vectors according to the invention. Quiescent or disrupted cells can also be used. Disrupted cells are to be understood for example as cells that have been made permeable by treatment with for example solvents, or cells that have been broken up by enzyme treatment, by mechanical treatment (e.g. French press or ultrasound) or by some other method. The resultant raw extracts are suitable for the method according to the invention. Purified or partially purified enzymes can also be used for the method. Immobilized microorganisms or enzymes are also suitable.

If free organisms or enzymes are used for the method according to the invention, prior to extraction it is desirable for these to be separated, for example by filtration or centrifugation.

If a two-phase (aqueous/organic) reaction medium is used, this facilitates product isolation, as the valuable product can dissolve preferentially in the organic phase. For example, the two-phase system is formed using in particular a solvent that is essentially immiscible with water, e.g. an ether.

Conversely, if a single-phase reaction medium is used in the enzymatic process step, the resultant product can be obtained from the aqueous reaction solution by extraction or distillation or advantageously by extraction and distillation. The extraction can be repeated several times to increase the yield. Examples of suitable extractants are solvents, such as toluene, methylene chloride, butyl acetate, diisopropyl ether, benzene, MTBE or ethyl acetate, without being limited to these.

After concentration of the organic phase by evaporation, the products can as a rule be obtained at good chemical purities, i.e. at more than 80%, 90%, 95% or 99% chemical purity. After extraction, however, the organic phase with the product can also only be partially concentrated by evaporation, and the product can be crystallized out. For this, advantageously the solution is cooled to a temperature from 0° C. to 10° C. Crystallization can also take place directly from the organic solution or from an aqueous solution. The crystallized product can be taken up again in the same or in a different solvent for repeat crystallization, and can be crystallized again. With the subsequent advantageous crystallization, carried out at least once, the enantiomeric purity of the product can if necessary be further increased.

In the aforementioned processing steps, the product of the method according to the invention can be isolated in yields from 60 to 100%, preferably from 80 to 100%, especially preferably from 90 to 100%, based on the substrate used for the reaction. The product isolated is characterized by a high chemical purity of >90%, preferably >95%, especially preferably >98%. Furthermore, the products have a high enantiomeric purity, which can advantageously be further increased if necessary by crystallization.

The method according to the invention can be operated batchwise, semi-batchwise or continuously.

The method can be carried out advantageously in bioreactors, as described for example in Biotechnology, Vol. 3, 2nd edition, Rehm et al., Eds., (1993) in particular Chapter II.

The above description and the following examples only serve to explain the invention. The numerous possible modifications that are obvious to a person skilled in the art are also covered by the invention.

Experimental Section:

Example 1

Synthesis of HCAP, 2 (in Ethyl Acetate)

A 6000-ml Miniplant reactor with impeller stirrer, baffle, thermometer and dropping funnel is charged with 435.68 g (3.20 mol) of 3-hydroxyacetophenone in 410.11 g (12.80 mol) of methanol and 1200 ml ethyl acetate. At 20-30° C., with cooling, 691.05 g (5.12 mol) of sulfuryl chloride is added dropwise to this solution within 2 h. After the dropwise addition, the mixture is stirred for a further hour at room temperature. Then the mixture is hydrolyzed at room temperature with 1600 ml $H_2O$ and the resultant two-phase mixture is separated. The aqueous phase is extracted once more with 800 ml ethyl acetate. The methanol and the ethyl acetate are distilled from the combined organic phases by means of a distillation bridge. Simultaneously, 1880 ml isopropanol is added dropwise to the distillation sump. We obtain 2462.5 g of a 17.3% isopropanolic solution of the valuable product, which corresponds to a content of 426 g (2.51 mol). The yield is therefore 78%.

Example 2

Synthesis of HCAP, 2 (in Dichloromethane)

A 2000-ml Miniplant reactor with impeller stirrer, baffle, thermometer and dropping funnel is charged with 204.23 g (1.50 mol) of 3-hydroxyacetophenone in 192.24 g (6.00 mol) of methanol and 1050 ml of $CH_2Cl_2$. At 20-30° C. with cooling, 283.44 g (2.10 mol) of sulfuryl chloride is added dropwise to this solution within 2 hours. After the dropwise addition, the mixture is stirred for a further hour at room temperature. Then the mixture is hydrolyzed at room temperature with 400 ml $H_2O$ and the resultant two-phase mixture is separated. After phase separation, the methanol and the $CH_2Cl_2$ are distilled from the organic phase by means of a distillation bridge at normal pressure. Simultaneously, 880 ml of isopropanol is added dropwise at the same rate. We obtain 837.78 g of a 25.7% isopropanolic solution of the valuable product, which corresponds to a content of 215 g (1.26 mol). The yield is therefore 84%.

Example 3

Synthesis of HCPE, 3

A ketone 2, prepared as in example 1 or 2, is reduced biocatalytically to R-3. For this, in a suitable stirred vessel, 1 mM $MgCl_2$, 0.02 mM nicotinamide adenine dinucleotide (NAD) and 282 g isopropanol, which also serves as sacrificial alcohol for cofactor regeneration, are dissolved in 1.44 L aqueous potassium phosphate buffer (50 mM, pH 7). Cells of recombinant *Escherichia coli* (corresponding to 3.75 g bio dry weight), which overproduce a stereoselective dehydrogenase (E.C. 1.1.1.1), are used as catalyst. The production of a suitable biocatalyst is described in WO 2005/108590, example 1-3, to which reference is expressly made hereby. The aqueous phase is covered with 1.3 kg MtBE. 292.8 g of 2 (as isopropanolic solution) is added to the reaction mixture. The concentration of 2 in the reaction mixture should not exceed 50 mM. The reaction can be monitored by achiral or chiral chromatography.

After the reaction, the organic phase and the aqueous phase separate owing to their different specific gravities. The valuable product R-3 is mainly in the MtBE phase.

Example 4

Synthesis of Phenylephrine, 4

Dissolve 15 g (86.9 mmol) of compound R-3 in 85 ml THF and react in the pressure autoclave at 90° C. with 13.5 g (435 mmol) of methylamine. Leave to react until the educt has been converted completely (approx. 5 hours). Then cool to room temperature and concentrate the resultant suspension by evaporation. On adding 100 g water, the free base of the valuable product is precipitated and isolated. We obtain 12.85 g (76.8 mmol, 88%) of phenylephrine free base.

---

The invention claimed is:

1. A method of production of substituted, optically active alcohols of formula IV

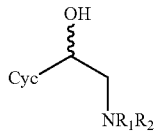

(IV)

in which

Cyc stands for a mono- or polynuclear, saturated or unsaturated, carbocyclic or heterocyclic, optionally singly or multiply substituted ring, which has at least one free hydroxyl group, and $R_1$ and $R_2$ independently of one another stand for H or an optionally singly or multiply substituted alkyl residue;

or of salts of this compound; in each case in stereoisomerically pure form or as a mixture of stereoisomers, wherein a) a ketone of formula I

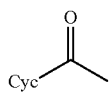

(I)

in which Cyc has the meanings stated above, is reacted in the presence of an aliphatic alcohol with a halogenating agent to a halogenated compound of formula II

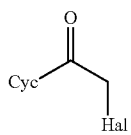

(II)

in which Cyc has the meanings stated above and Hal stands for a halogen atom;

b) the resultant compound of formula II is reduced enzymatically by an ADH enzyme comprising a polypeptide sequence selected from the group consisting of
  (i) the amino acid sequence of SEQ ID NO: 2, and
  (ii) the amino acid sequence having at least 95% sequence identity to the amino acid sequence of SEQ ID NO: 2 to the alcohol of formula III

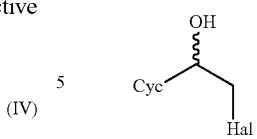

(III)

in which Cyc and Hal have the meanings stated above; and
c) the resultant alcohol of formula III is reacted with an amine of formula $HNR_1R_2$, in which $R_1$ and $R_2$ have the meanings stated above, to the compound of formula IV.

2. The method as claimed in claim 1, wherein the reaction in stage a) takes place in the presence of 1 to 10 molar equivalents of alcohol per mol of alkanone of formula I.

3. The method as claimed in claim 1, wherein the chemical reaction in stage c) takes place in solution in an open-chain or cyclic ether.

4. The method as claimed in claim 1, wherein the reaction in stage
  b) is carried out with addition of reduction equivalents, in particular NADH or NADPH and optionally the reduction equivalents consumed during the reaction are regenerated.

5. The method as claimed in claim 4, wherein the regeneration is carried out enzymatically, electrochemically or electro-enzymatically.

6. The method as claimed in claim 5, wherein the regeneration takes place enzymatically and the regenerating enzyme is selected from ADH and dehydrogenases different from ADH, in particular glucose dehydrogenases, formate dehydrogenases, phosphite dehydrogenases.

7. The method as claimed in claim 1, wherein the reaction in stage b) takes place in the presence of a microorganism, which expresses the ADH naturally or recombinantly, or in the presence of a fraction derived therefrom, containing the ADH, or in the presence of an extract derived therefrom, containing the ADH.

8. The method as claimed in claim 7, wherein the reaction in stage b) takes place in the presence of an ADH-producing microorganism, which is selected from bacteria of the families Enterobacteriaceae, Pseudomonadaceae, Rhizobiaceae, Lactobacillaceae, Streptomycetaceae, Rhodococcaceae, Rhodocyclaceae and Nocardiaceae, or in the presence of an ADH-containing fraction or extract derived therefrom.

9. The method as claimed in claim 8, wherein the microorganism is a recombinant microorganism, which is transformed with a nucleic acid construct that codes for the ADH.

10. The method as claimed in claim 1, wherein stage b) is carried out in a two-phase liquid reaction medium.

11. The method as claimed in claim 10, wherein an aqueous-organic reaction medium is used, and both the educt of formula II and the product of formula III are more soluble in the organic phase than in the aqueous phase.

12. The method as claimed in claim 1, in which Cyc stands for a 3-hydroxyphenyl residue and Hal stands for a chlorine atom.

* * * * *

```
                        SEQUENCE LISTING

<160> NUMBER OF SEQ ID NOS: 2

<210> SEQ ID NO 1
<211> LENGTH: 750
<212> TYPE: DNA
<213> ORGANISM: Aromatoleum aromaticum
<220> FEATURE:
<223> OTHER INFORMATION: Aromatoleum aromaticum EbN1
<220> FEATURE:
<221> NAME/KEY: CDS
<222> LOCATION: (1)..(750)

<400> SEQUENCE: 1 atg acg caa aga ctg aag gac aag ctt gca gta att acc ggc ggt gcc      48
Met Thr Gln Arg Leu Lys Asp Lys Leu Ala Val Ile Thr Gly Gly Ala
1               5                   10                  15 aac ggc atc ggg cgg gca att gcg gag cga ttt gcg gtc gaa ggt gcc      96
Asn Gly Ile Gly Arg Ala Ile Ala Glu Arg Phe Ala Val Glu Gly Ala
                20                  25                  30 gac atc gca atc gcg gat ctg gtg ccg gcc ccg gaa gcc gag gca gca     144
Asp Ile Ala Ile Ala Asp Leu Val Pro Ala Pro Glu Ala Glu Ala Ala
            35                  40                  45 atc agg aac ctc ggt cgg cgc gtt ctg acc gtg aag tgc gat gtc tcg     192
Ile Arg Asn Leu Gly Arg Arg Val Leu Thr Val Lys Cys Asp Val Ser
        50                  55                  60 caa cct ggc gac gta gaa gca ttc gga aag cag gtc atc tcc acg ttt     240
Gln Pro Gly Asp Val Glu Ala Phe Gly Lys Gln Val Ile Ser Thr Phe
65                  70                  75                  80 ggt cgc tgc gac atc ctc gtc aac aac gcg gga att tac ccg ctg att     288
Gly Arg Cys Asp Ile Leu Val Asn Asn Ala Gly Ile Tyr Pro Leu Ile
                85                  90                  95 cct ttt gac gag ctg acc ttt gaa cag tgg aag aaa aca ttc gag atc     336
Pro Phe Asp Glu Leu Thr Phe Glu Gln Trp Lys Lys Thr Phe Glu Ile
                100                 105                 110 aac gtc gat tca ggt ttt ctt atg gcg aag gct ttt gtc ccc ggg atg     384
Asn Val Asp Ser Gly Phe Leu Met Ala Lys Ala Phe Val Pro Gly Met
            115                 120                 125 aag agg aac ggg tgg gga cgc atc atc aac ctg act tcg acg aca tat     432
Lys Arg Asn Gly Trp Gly Arg Ile Ile Asn Leu Thr Ser Thr Thr Tyr
        130                 135                 140 tgg cta aag atc gag gcg tat acc cat tac atc agc acg aaa gcg gca     480
Trp Leu Lys Ile Glu Ala Tyr Thr His Tyr Ile Ser Thr Lys Ala Ala
145                 150                 155                 160 aac ata ggc ttt acc cgc gcc ctt gcc tcg gac ctg ggg aag gac gga     528
Asn Ile Gly Phe Thr Arg Ala Leu Ala Ser Asp Leu Gly Lys Asp Gly
                165                 170                 175 atc act gtt aac gcc atc gcg ccg agc ctt gtc cgc acg gca aca acc     576
Ile Thr Val Asn Ala Ile Ala Pro Ser Leu Val Arg Thr Ala Thr Thr
            180                 185                 190 gaa gct tct gca ttg tcc gcg atg ttc gac gtg ctg cca aac atg ctt     624
Glu Ala Ser Ala Leu Ser Ala Met Phe Asp Val Leu Pro Asn Met Leu
        195                 200                 205 cag gcg att ccg cgt ctt cag gtg ccc ctg gat ctg acg ggc gca gct     672
Gln Ala Ile Pro Arg Leu Gln Val Pro Leu Asp Leu Thr Gly Ala Ala
    210                 215                 220
```

```
gcg ttc ctg gct tcc gat gac gcc agt ttt att aca ggc cag acg ctc      720
Ala Phe Leu Ala Ser Asp Asp Ala Ser Phe Ile Thr Gly Gln Thr Leu
225                 230                 235                 240 gcg gtt gat ggc ggt atg gtg aga cac tga                              750
Ala Val Asp Gly Gly Met Val Arg His
                245
```

<210> SEQ ID NO 2
<211> LENGTH: 249
<212> TYPE: PRT
<213> ORGANISM: Aromatoleum aromaticum
<220> FEATURE:
<223> OTHER INFORMATION: Aromatoleum aromaticum EbN1

<400> SEQUENCE: 2

```
Met Thr Gln Arg Leu Lys Asp Lys Leu Ala Val Ile Thr Gly Gly Ala
1               5                   10                  15

Asn Gly Ile Gly Arg Ala Ile Ala Glu Arg Phe Ala Val Glu Gly Ala
            20                  25                  30

Asp Ile Ala Ile Ala Asp Leu Val Pro Ala Pro Glu Ala Glu Ala Ala
        35                  40                  45

Ile Arg Asn Leu Gly Arg Arg Val Leu Thr Val Lys Cys Asp Val Ser
    50                  55                  60

Gln Pro Gly Asp Val Glu Ala Phe Gly Lys Gln Val Ile Ser Thr Phe
65                  70                  75                  80

Gly Arg Cys Asp Ile Leu Val Asn Asn Ala Gly Ile Tyr Pro Leu Ile
                85                  90                  95

Pro Phe Asp Glu Leu Thr Phe Glu Gln Trp Lys Lys Thr Phe Glu Ile
            100                 105                 110

Asn Val Asp Ser Gly Phe Leu Met Ala Lys Ala Phe Val Pro Gly Met
        115                 120                 125

Lys Arg Asn Gly Trp Gly Arg Ile Ile Asn Leu Thr Ser Thr Thr Tyr
    130                 135                 140

Trp Leu Lys Ile Glu Ala Tyr Thr His Tyr Ile Ser Thr Lys Ala Ala
145                 150                 155                 160

Asn Ile Gly Phe Thr Arg Ala Leu Ala Ser Asp Leu Gly Lys Asp Gly
                165                 170                 175

Ile Thr Val Asn Ala Ile Ala Pro Ser Leu Val Arg Thr Ala Thr Thr
            180                 185                 190

Glu Ala Ser Ala Leu Ser Ala Met Phe Asp Val Leu Pro Asn Met Leu
        195                 200                 205

Gln Ala Ile Pro Arg Leu Gln Val Pro Leu Asp Leu Thr Gly Ala Ala
    210                 215                 220

Ala Phe Leu Ala Ser Asp Asp Ala Ser Phe Ile Thr Gly Gln Thr Leu
225                 230                 235                 240

Ala Val Asp Gly Gly Met Val Arg His
                245
```